( 12 ) United States Patent
Puhl et al.

(10) Patent No.: US 6,469,056 B1
(45) Date of Patent: Oct. 22, 2002

(54) PHARMACEUTICALLY ACTIVE COMPOUNDS, THEIR PREPARATION AND USE AS ECE-INHIBITORS

(75) Inventors: Michael Puhl, Eschborn (DE); Johann-Christian Zechel, Nussloch (DE); Klaus Ditrich, Gönnheim (DE); Heinz Hillen, Hassbloch (DE); Tanja Kohl, Ellerstadt (DE); Melanie Erhardt, Fussgönheim (DE); Stefan Hergenröder, Mainz (DE); Claus Otto Markert, Schifferstadt (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/529,181

(22) PCT Filed: Sep. 18, 1998

(86) PCT No.: PCT/EP98/05945

§ 371 (c)(1),
(2), (4) Date: Apr. 10, 2000

(87) PCT Pub. No.: WO99/19320

PCT Pub. Date: Apr. 22, 1999

(30) Foreign Application Priority Data

Oct. 14, 1997 (DE) .......................... 197 45 146

(51) Int. Cl.[7] .................. A61K 31/27; A61K 31/16; C07C 59/74; C07C 205/00
(52) U.S. Cl. ................ 514/480; 514/566; 514/569; 514/616; 562/459; 568/306
(58) Field of Search .................. 568/306; 562/459; 514/480, 566, 569, 616

(56) References Cited

U.S. PATENT DOCUMENTS 5,610,177 A    3/1997  Doherty et al.

FOREIGN PATENT DOCUMENTS

| WO | 94/15956 | 7/1994 |
| WO | 94/22906 | 10/1994 |
| WO | 95/00537 | 1/1995 |
| WO | 95/12611 | 5/1995 |

OTHER PUBLICATIONS

CA 133:8885, Tsubone, 2000.*
CA 124:105575, Leftheris, 1996.*
Nature 348, 732, (1990)Sakurai et al.
Nature, 299, 555–557, (1982), Szelke et al.
J.Pharmacol., Exp. Ther, 1989, 250,624, Sybertz et al.
J.Med.Chem., 1995, 38, 3462, Hruby et al.
J.Med.Chem.,1987, 30, 1162, Coy et al.
Tetrahedron, 44, 1988, 835, Coy et al.
J.Am. Chem. Soc. 1995, 117, 7029.
J.Med.Chem., vol. 40, 1997:2228–2240, Cody et al.
Bioorg.Chem.Lett, vol. 7, No. 10, 1996:1151–56,Waelchli.
PeptideRes., Doulut et al., 30–38,vol. 5,No. 1,1992.
Can.J.Chem., vol. 64,1986:12396–1399, Ahmed et al.
J.Med.Chem.,vol. 33, No. 2, 1990:838–845,Kaltenbroun.
J.Med.Chem.,vol. 39, No. 1,1996:224–236,Leftheris et al.
J.Med.Chem.,1996,39, 224–236,Leftheris et al.
Nature,344, 114(1990).
Stroke 25, 904(1994),Cosentino.
Nature 365,759 (1993)Clozel et al.
J.Mol.amdCell.Card., 27, A234(1995),Goldstein.
Cancer Res. 56, 663(1996),Nelson et al.
Nature Medicine 1, 944(1995)Nelson et al.
Nature 348, 70, (1990)Arai et al.
NewEng.J.Med.,322,205(1989).
New.Eng.J.Med., 328,1732(1993).
Nephron 66,33,373(1994),Takahashi et al.
Nature 332, 411–415, 1988,Yanagisawa et al.
FEPS Ltrs. 231,440–444,1988, Yanagisawa et al.
Biochem.Biophys.Res.Com.154,868–875,1988,Hirata et al.
J.Vas.Med.Bio. 2, 207(1990).
JAMA,264,2868(1990).

* cited by examiner

*Primary Examiner*—D. Margaret Seaman
(74) *Attorney, Agent, or Firm*—Keil & Weinkauf

(57) ABSTRACT

Pharmaceutically active compounds are prepared as described and used to produce pharmaceutical preparations for treating diseases.

10 Claims, No Drawings

PHARMACEUTICALLY ACTIVE COMPOUNDS, THEIR PREPARATION AND USE AS ECE-INHIBITORS

This application is a 371 of PCT/EP98/05945, filed Sep. 18, 1998.

The invention relates to novel pharmaceutically active compounds, their preparation and use for producing pharmaceutical preparations for treating diseases.

Endothelin is a peptide which is composed of 21 amino acids and is synthesized and released by vascular endothelium. Endothelin exists in three isoforms, ET-1, ET-2 and ET-3. "Endothelin" or "ET" hereinafter refers to one or all isoforms of endothelin. Endothelin is a potent vasoconstrictor and has a strong effect on vessel muscle tone. It is known that this vasoconstriction is caused by the binding of endothelin to its receptor (Nature, 332, 1988, 411–415; FEBS Letters, 231, 1988, 440–444 and Biochem. Biophys. Res. Commun., 154, 1988, 868–875).

Elevated or abnormal release of endothelin causes persistent vasoconstriction in peripheral, renal and cerebral blood vessels, which may lead to disorders. As reported in the literature, endothelin is involved in a number of disorders, these include: hypertension, acute myocardial infarct, pulmonary hypertension, Raynaud's syndrome, cerebral vasospasms, stroke, benign prostate hypertrophy, atherosclerosis, asthma and prostate cancer (J. Vascular Med. Biology 2, (1990) 207, J. Am. Med. Association 264, (1990) 2868, Nature 344, (1990) 114, N. Engl. J. Med. 322, (1989) 205, N. Engl. J. Med. 328, (1993) 1732, Nephron 66, (1994) 373, Stroke 25, (1994) 904, Nature 365, (1993) 759, J. Mol. Cell. Cardiol. 27, (1995) A234; Cancer Research 56, (1996) 663, Nature Medicine 1, (1995) 944).

At least two endothelin receptor subtypes, $ET_A$ and $ET_B$ receptors, have been described in the literature (Nature 348, (1990) 730, Nature 348, (1990) 732). Accordingly, substances which inhibit the binding of endothelin to one or to both receptors ought to antagonise the physiological effects of endothelin and therefore represent valuable drugs.

However, the disadvantage of these receptor antagonists is that endothelin has already formed and the effect of endothelin must be antagonized after its production. Substances which prevent formation of endothelin from its precursor, which is called big endothelin, intervene at an earlier stage in the effect of endothelin and thus represent a desired alternative to the endothelin receptor antagonists because they ought to have a more direct and better effect, as shown, for example, by inhibitors of ACE (ACE= "angiotensin converting enzyme", Szelke et al. Nature, 299, 555) or of ANP (ANP=,Sybertz et al., J. Pharmacol. Exp. Ther. 250, 1989, 624).

It is an object of the present invention to provide inhibitors of endothelin converting enzyme (=ECE).

We have found that this object is achieved by compounds of the formula I:

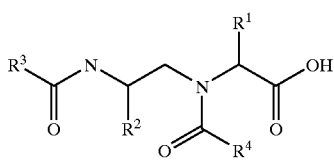
(I)

its physiolically active salts or combination thereof, where the substituents have the following meanings:

$R^1$ and $R^2$ independently of one another substituted or unsubstituted, branched or unbranched $C_1$–$C_8$-alkyl, $C_1$–$C_8$-alkylaryl or $C_1$–$C_8$-alkylhetaryl, substituted or unsubstituted aryl or hetaryl $R^3$ a group of the formula a, b or c:

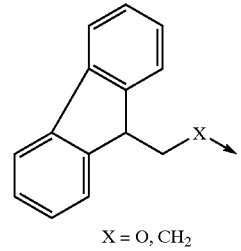
(a)

X = O, CH$_2$

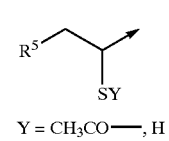
(b)

Y = CH$_3$CO—, H

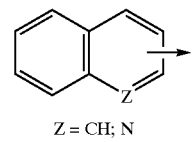
(c)

Z = CH; N $R^4$ substituted or unsubstituted $C_4$–$C_{14}$-aryl, $C_4$–$C_{14}$-hetaryl, with one or more rings containing one or more hetero atoms selected from the group of O, S and N, $R^5$ $C_1$–$C_8$-alkyl, $C_1$–$C_8$-alkylaryl, aryl or hetaryl.

The invention further relates to a process for preparing the abovementioned compounds of the formula I, which comprises condensing a compound of the formula II:

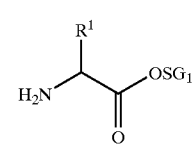
(II)

with a compound of the formula III

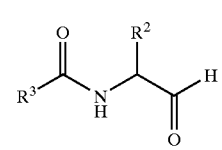
(III)

and reducing with a reducing agent to a compound of the formula IV:

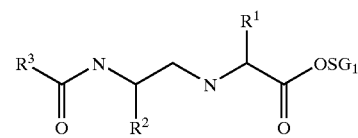
(IV)

and reacting with an acylating agent $R^4COCl$ (V) and eliminating the protective group $SG_1$ to give the abovementioned compounds of the formula I, where the substituents $R^1$, $R^2$, $R^3$ and $R^4$, have the meanings mentioned above, and $SG_1$ is a protective group.

The invention further relates to the use of compounds of the formula I for inhibiting endothelin converting enzyme (=ECE), for producing pharmaceutical preparations for treating diseases and to the use of these pharmaceutical preparations in combination with at least one other active substance or drug which lowers blood pressure.

The substituents $R^1$ and $R^2$ in the abovementioned formulae I, II, III and IV have the following meanings:

$R^1$ and $R^2$ independently of one another substituted or unsubstituted, branched or unbranched $C_1$–$C_8$-alkyl, $C_1$–$C_8$-alkylaryl or $C_1$–$C_8$-alkylhetaryl, substituted or unsubstituted aryl or hetaryl, where alkyl branched or unbranched $C_1$–$C_8$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl or n-octyl;

alkylaryl branched-chain or unbranched-chain $C_1$–$C_8$-alkylaryl such as $C_1$–$C_8$-alkylphenyl or $C_1$–$C_8$-alkylnaphthyl radicals, such as methylphenyl, ethylphenyl, propylphenyl, 1-methylethylphenyl, butylphenyl, 1-methylpropylphenyl, 2-methylpropylphenyl, 1,1-dimethylethylphenyl, pentylphenyl, 1-methylbutylphenyl, 2-methylbutylphenyl, 3-methylbutylphenyl, 2,2-dimethylpropylphenyl, 1-ethylpropylphenyl, hexylphenyl, heptylphenyl, octylphenyl, methylnaphthyl, ethylnaphthyl, propynaphthyl, 1-methylethylnaphthyl, butylnaphthyl, 1-methylpropylnaphthyl, 2-methylpropylnaphthyl, 1,1-dimethylethylnaphthyl, pentylnaphthyl, 1-methylbutylnaphthyl, 2-methylbutylnaphthyl, 3-methylbutylnaphthyl, 2,2-dimethylpropylnaphthyl, 1-ethylpropylnaphthyl, hexylnaphthyl, heptylnaphthyl or octylnaphthyl;

alkylhetaryl branched-chain or unbranched-chain $C_1$–$C_8$-alkylhetaryl radicals which [lacuna] simple or fused aromatic ring systems with one or more heteroaromatic 3- to 8-membered rings which may, where appropriate, contain one or more hetero atoms such as S, N or O;

aryl such as phenyl, naphthyl, anthranyl or phenanthryl;

hetaryl simple or fused aromatic ring systems with one or more heteroaromatic 5- to 8-membered rings which may, where appropriate, contain one or more heteroatoms such as S, N or O, such as thienyl, pyridyl or indoyl [sic].

All said radicals $R^1$ or $R^2$ may, where appropriate, be substituted by one or more of the radicals —$NH_p(C_1$–$C_8$-alkyl$)_{2-p}$, —$QH_n(C_1$–$C_8$-alkyl$)_{1-n}$, —SS-t-butyl, —CN, —$NO_2$ or halogen such as fluorine, chlorine, bromine or iodine, where p is 0, 1 or 2, Q is sulfur or oxygen, n is 0 or 1, and $C_1$–$C_8$-alkyl has the abovementioned meaning.

Preferred radicals for $R^1$ and $R^2$ are those derived from natural or unnatural amino acids, it being possible for functional groups in these radicals to be protected or unprotected. Since the radicals $R^1$ and $R^2$ are advantageously derived from natural or unnatural amino acids, the stereo- centers adjacent to the radicals may exist both in the D and in the L configuration (=R- or S-form). Further preferred radicals for $R^1$ and $R^2$ are substituted or unsubstituted, branched or unbranched $C_1$–$C_4$-alkyl, $C_1$–$C_4$-alkylaryl or $C_1$–$C_4$-alkylhetaryl, substituted or unsubstituted aryl or hetaryl, and $C_1$–$C_4$-alkylaryl is particularly preferred.

It is possible in principle, in a less preferred form, for the radicals $R^1$ or $R^2$ also to be hydrogen. However, compounds with these radicals show only very little or no biological effect.

The substituent $R^3$ in the abovementioned formulae I, III and IV has the following meaning:

$R^3$ a group of the formula a, b or c:

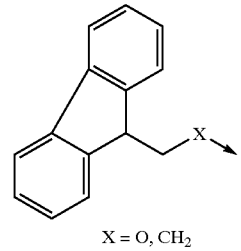

(a)

$X = O, CH_2$

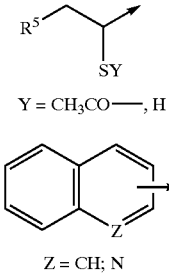

(b)

$Y = CH_3CO—, H$

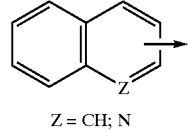

(c)

$Z = CH; N$

Formulae a, b and c may, where appropriate, have other substituents. $R^5$ in formula b has the meaning mentioned below.

The substituent $R^4$ in the abovementioned formulae I and V has the following meaning:

$R^4$ substituted or unsubstituted $C_4$–$C_{14}$-aryl, $C_4$–$C_{14}$-hetaryl with one or more rings containing one or more hetero atoms selected from the group of O, S and N, where $C_4$–$C_{14}$-aryl such as phenyl, naphthyl, anthranyl or phenanthryl;

$C_4$–$C_{14}$-hetaryl simple or fused aromatic ring systems with one or more heteroaromatic 5- to 8-membered rings may, where appropriate, contain one or more heteroatoms such as S, N or O, such as thienyl, pyridyl or indoyl.

All said radicals $R^4$ may, where appropriate, be substituted by one or more of the following radicals: branched-chain or unbranched-chain $C_1$–$C_4$-alkyl, $C_6$–$C_{14}$-aryl, —$COOR^6$, —$NH_p(C_1$–$C_8$-alkyl$)_{2-p}$, —$QH_n(C_1$–$C_8$-alkyl$)_{1-n}$, —SS-t-butyl, —CN, —$NO_2$ or halogen such as fluorine, chlorine, bromine or iodine, where $R^6$ is H or $C_1$–$C_8$alkyl, p is 0, 1 or 2, Q is sulfur or oxygen, n is 0 or 1, and $C_1$–$C_8$-alkyl, $C_1$–$C_4$-alkyl or $C_6$–$C_{14}$-aryl have the abovementioned meanings.

The substituent $R^5$ in the abovementioned formulae b has the following meaning:

$R^5$ $C_1$–$C_8$-alkyl, $C_1$–$C_8$-alkylaryl, aryl or hetaryl, alkyl branched or unbranched $C_1$–$C_8$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl or n-octyl;

alkylaryl branched-chain or unbranched-chain $C_1$–$C_8$-alkylaryl, such as $C_1$–$C_8$-alkylphenyl or $C_1$–$C_8$-alkylnaphthyl radicals, such as methylphenyl, ethylphenyl, propylphenyl, 1-methylethylphenyl, butylphenyl, 1-methylpropylphenyl, 2-methylpropylphenyl, 1,1-dimethylethylphenyl, pentylphenyl, 1-methylbutylphenyl, 2-methylbutylphenyl, 3-methylbutylphenyl, 2,2-dimethylpropylphenyl, 1-ethylpropylphenyl, hexylphenyl, heptylphenyl, octylphenyl, methylnaphthyl, ethylnaphthyl, propynaphthyl, 1-methylethylnaphthyl, butylnaphthyl, 1-methylpropylnaphthyl, 2-methylpropylnaphthyl, 1,1-dimethylethylnaphthyl, pentylnaphthyl, 1-methylbutylnaphthyl, 2-methylbutylnaphthyl, 3-methylbutylnaphthyl, 2,2-dimethylpropylnaphthyl, 1-ethylpropylnaphthyl, hexylnaphthyl, heptylnaphthyl or octylnaphthyl;

aryl such as phenyl, naphthyl, anthranyl or phenanthryl;

hetaryl simple or fused aromatic ring systems with one or more heteroaromatic 5- to 8-membered rings which may, where appropriate, contain one or more hetero atoms such as S, N, or O, such as thienyl, pyridyl or indoyl;

The radical $R^5$ may, where appropriate, have further substituents.

The compounds according to the invention may be in the form of the free compounds or in the form of their physiologically active salts, their tautomeric and isomeric forms or in the form of the combination of the free compounds and the various salts. The compounds according to the invention also include the enantiomerically pure or diastereomerically pure compounds, their salts or their mixtures.

The enantiomeric or diastereomeric forms of the compounds according to the invention can be purified or prepared in a manner known per se for example by forming diastereomeric salts, by chiral chromatographic methods or by stereoselective syntheses.

The compounds according to the invention are prepared by a process known to the skilled worker as disclosed, for example, in Hruby et al. (J. med. Chem 38, 1995, 3462), Coy et al. (J. med. Chem. 30, 1987, 1162) or Coy et al. (Tetrahedron, 44, 1988, 835) and therefore requires no further explanation. This advantageously entails an amino acid derivative of the formula II which is suitably protected on the carboxyl group being condensed with an amino aldehyde of the formula III to give the imine, and then reducing the latter in situ with, for example, $NaBH_3CN$ with the addition of acid to give the amine of the formula IV (see Reaction scheme I).

Reaction scheme I: Synthesis of compounds of the formula I:

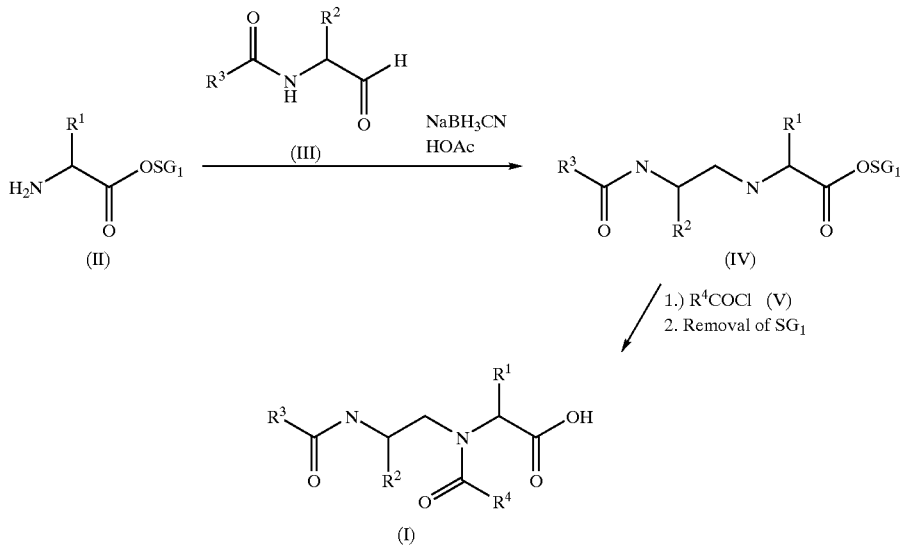

Protective groups suitable as protective group $SG_1$ are all those known to the skilled worker in protein synthesis, such as t-butyl, benzyl, trityl, methyl or else polymer-linked protective groups in the form of the commercially available polystyrene resins such as 2-chlorotrityl chloride resin or Wang resin (supplied by Bachem or Novabiochem). Preferred protective groups are t-butyl and 2-chlorotrityl-resins.

The conversion into the imine and the in situ reduction take place as described in the literature (V. J. Hruby et al. J. med. Chem. 38, 1995, 3462, D. H. Coy et al. J. med. Chem., 30, 1987, 1162 and D. H. Coy et al. Tetrahedron 44 1988 835), it being possible and advantageous to add trimethyl orthoformate for the imine formation as described by Gallop et al. (J. Am. Chem. Soc. 117, 1995, 7029).

Further derivatization of compounds of the formula IV to give compounds of the formula I preferably takes place with an acid chloride with addition of base; this reaction step also requires no further explanation and is known to the skilled worker.

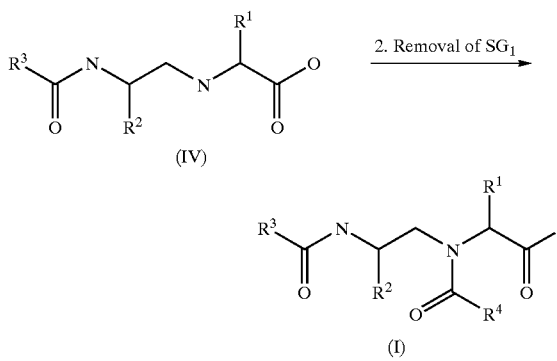

Conversion of IV into I is preferably carried out in a mixture of pyridine and methylene chloride (about 1:1) at from 0 to 100° C., preferably at 20 to 60° C., with a 2 to 10-fold excess of the acid chloride.

After completion of the synthesis, the compounds of the formula I are, if required, purified by conventional chromatographic methods, for example by preparative FPLC or HPLC which is customary in the purification of proteins and peptides.

Replacement of a peptide linkage by a $CH_2NH$ group in the compounds according to the invention results in these compounds having increased stability toward peptide-cleaving enzymes and thus showing longer biological activity.

Since the side chains are unaffected by this modification, the compounds according to the invention closely resemble true peptides. They are thus to be regarded as stable synthetic analogs of the natural substrates, because the conformation of the substances is altered only inconsiderably or not at all by this slight change in the molecules.

The compounds according to the invention are very selective inhibitors of endothelin converting enzyme with activities in the pm range and can be used for this purpose. No inhibition of other metalloproteases such as ACE (=angiotensin converting enzyme), NEP 24.11 (=neutral endopeptidase 24.11) or the matrix metalloproteases (=MMP) MMP-1, MMP-3 or MMP-9 was detectable in this range; thermolysin, papain and thrombin do not accept these compounds as substrates, nor are they inhibited by them. The advantage of such a selective class of inhibitors is obvious: on the one hand, there is no intervention in other enzymatic processes, so that no unwanted side effects are to be expected either, and, on the other hand, these compounds are also very stable to enzymatic degradation because they cannot be degraded by other proteases in a nonspecific reaction. It is therefore very likely that they can be administered in very low doses, which means that the probability of side effects by, for example, degradation products of the compounds can be further reduced.

The compounds according to the invention, their stereoisomeric forms and/or physiologically active salts, and their tautomeric or isomeric forms, are suitable for producing pharmaceutical preparations for treating diseases, preferably for producing medicines for treating diseases associated with vasoconstriction or other biological effects of endothelin. The enantiomerically pure or diastereomerically pure compounds are preferably used as active substance.

The compounds of the present invention provide a novel therapeutic potential for the treatment of hypertension, pulmonary hypertension, myocardial infarct, chronic heart failure, angina pectoris, acute/chronic kidney failure, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis after angioplasty, benign prostate hyperplasia, ischemic and intoxication-induced kidney failure or hypertension, cyclosporin-induced kidney failure, metastasis and growth of mesenchymal tumors, cancer, prostate cancer, contrast agent-induced kidney failure, pancreatitis and gastrointestinal ulcers.

The compounds according to the invention are preferably administered in the form of pharmaceutical preparations such that the release takes place under the conditions prevailing in particular compartments of the body, eg. in the stomach, intestine, bloodstream or liver.

The invention further relates to combination products consisting of inhibitors of the formula I according to the invention and inhibitors of the renin-angiotensin system. Inhibitors of the renin-angiotensin system are renin inhibitors, angiotensin II antagonists and, in particular, angiotensin converting enzyme (ACE) inhibitors.

The combinations can be administered in a single pharmaceutical form or temporally and spatially separate.

Concerning the dosage and mode of administration, the factors to be taken into account are the same as for the corresponding single substances.

These combination products are particularly suitable for the treatment and prevention of hypertension and its sequelae, and for treating heart failure.

The compounds according to the invention can be administered orally or parenterally (subcutaneously, intravenously, intramuscularly, intraperitoneally) in a conventional way. Administration can also take place with vapors or sprays through the nasopharyngeal space.

The dosage depends on the age, condition and weight of the patient and on the mode of administration.

The novel compounds of the invention can be used in conventional solid or liquid pharmaceutical forms, eg. as uncoated or (film-)coated tablets, capsules, powders, granules, suppositories, solutions, ointments, creams or sprays. These are produced in a conventional way. The active substances can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The administration forms obtained in this way normally contain from 0.1 to 90% by weight of the active substance.

The combination of a calcium antagonist with the inhibitors according to the invention can be used for treating disorders based on vasoconstriction or associated with pathological vasoconstriction. Examples are: all types of high blood pressure (including pulmonary hypertension), coronary heart disease, heart failure, renal and myocardial ischemia, acute and chronic renal insufficiency.

Because of the potentiation of the effect of the individual components, combination of the two classes of active substances is an ideal addition. Another advantage is that the reduction in dose means that unwanted side effects occur more rarely.

The combinations according to the invention are generally administered orally, for example in the form of uncoated or (lacquer-)coated tablets, hard and soft gelatin capsules, solutions, emulsions or suspensions. However, administration can also take place rectally, eg. in the form of suppositories, or parenterally, eg. in the form of solutions for injection. The active substance can be administered in the form of products which contain both active substances together, such as tablets or capsules, or separately as ad hoc combination of single substances which can be administered simultaneously or sequentially.

Uncoated and (lacquer-)coated tablets and hard gelatin capsules can be produced by processing a combination according to the invention with pharmaceutically inert inorganic or organic excipients. Excipients which can be used for uncoated and coated tablets and hard gelatin capsules are lactose, cornstarch or derivatives thereof, talc, stearic acid or its salts. Excipients suitable for soft gelatin capsules are vegetable oils, waxes, fats, semisolid and liquid polyols.

Examples of suitable excipients for producing solutions and syrups are water, polyols, sucrose, invert sugar, glucose and the like. Suitable excipients for solutions for injection are water, alcohols, polyols, glycerol, vegetable oils. Suitable excipients for suppositories are natural or hardened oils, waxes, fats, semiliquid or liquid polyols and the like.

The pharmaceutical preparations may additionally contain preservatives, solubilizers, stabilizers, wetting agents, emulsifiers, sweeteners, colorants, flavourings, salts to alter the osmotic pressure, buffers, coating agents and/or antioxidants.

EXAMPLES

Example 1

Synthesis of Compounds 1a to 1k a. 0.4 mmol of phenylalanine with C-terminal protection by the 2-Cl-trityl-resin (2a) was shaken with 0.75 mmol of N-Fmoc- phenylalaninal (3a) (R=CH$_2$Ph, R$^3$=Fmoc) in 9 ml of 99:1 DMF/HOAc for 0.5 h. Then NaBH$_3$CN was added in portions until the ninhydrin test indicated that no free primary amino group was present. The solid (4a) was then filtered off with suction, washed with DMF, isopropanol and methylene chloride and dried under reduced pressure.

0.4 mmol of (4a) was shaken with a catalytic amount of DMAP (=4-dimethylaminopyridine) and 2 mmol of 2-thiophenecarbonyl chloride in about 10 ml of 1/1 pyridine/methylene chloride until the ninhydrin test indicated no secondary amino group present. The product was filtered off with suction and washed with DMF and methylene chloride, and the polymeric protective group was removed as follows: (4a) was shaken in about 10 ml of a 1/1/8 mixture of acetic acid, trifluoroethanol and methylene chloride for 1 h, and the solution containing 1a was filtered off and concentrated (reaction scheme II).

Reaction scheme II: Synthesis of compound (1a)

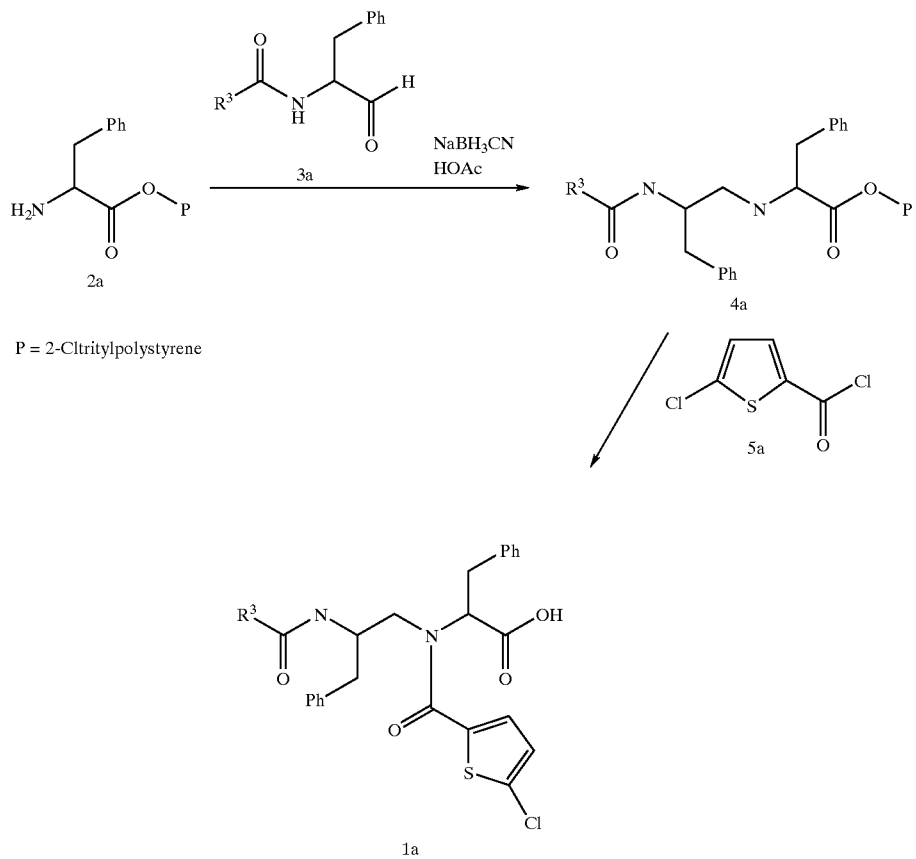

The following compounds 1b to 1e and 1g to 1k were prepared in a similar way. The stated molecular weights were determined by molecular spectroscopic methods.
| No. | Formula | Molecular weight (MS-ESI or APCI) |
|---|---|---|
| 1a | 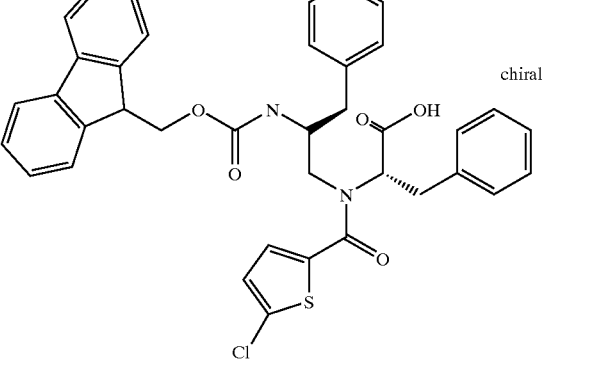 | 664 |
| 1b | 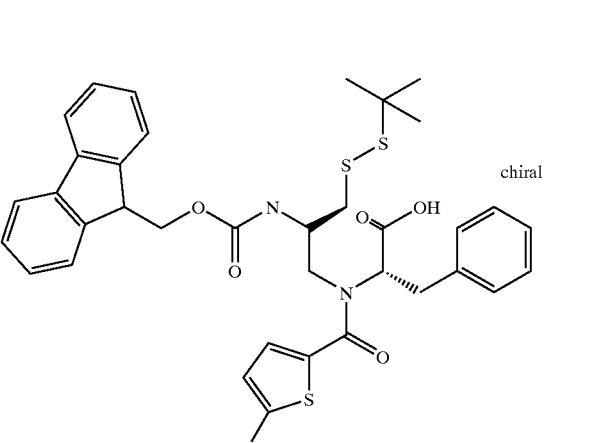 | 708 |
| 1c | 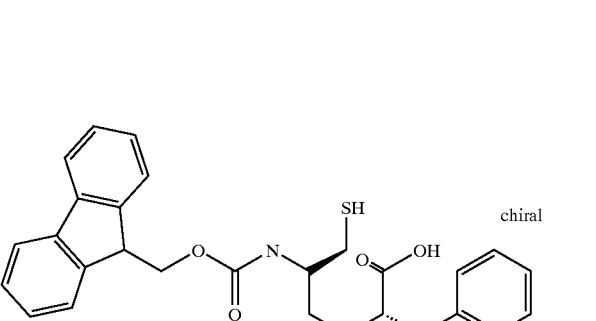 | 620 |

-continued
| No. | Formula | Molecular weight (MS-ESI or APCI) |
|---|---|---|
| 1d | 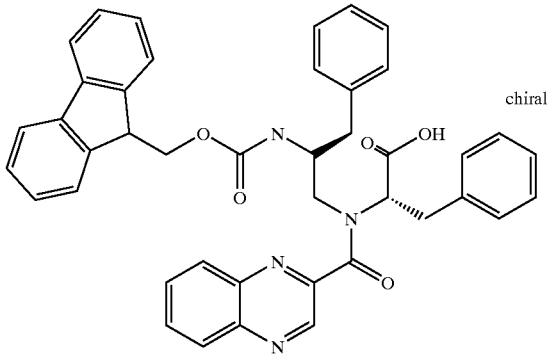 chiral | 676 |
| 1e | 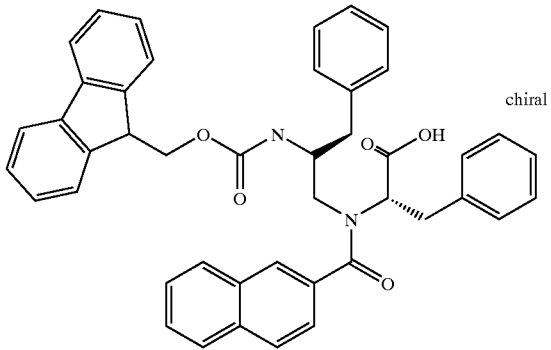 chiral | 674 |
| 1g | 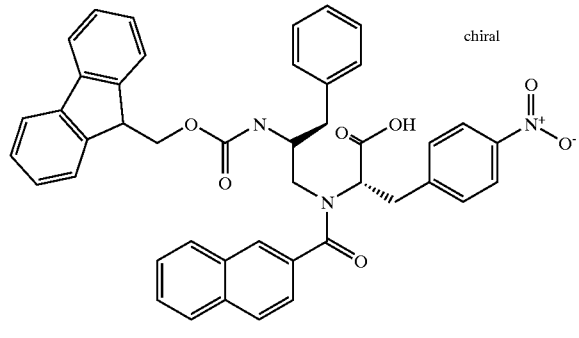 chiral | 719 |
| 1h | 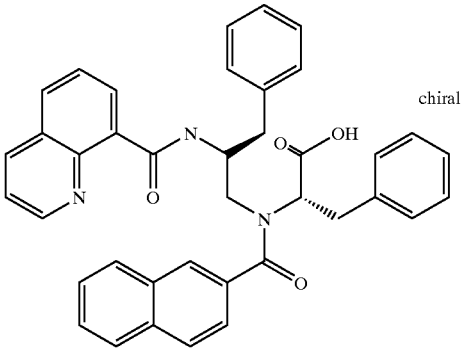 chiral | 607 |

-continued

| No. | Formula | Molecular weight (MS-ESI or APCI) |
|---|---|---|
| 1i | | 596 |
| 1j | | 630 |
| 1k | | 616 |

Example 2
ECE Inhibitor Tests, IC$_{50}$ Determinations

Inhibitors of endothelin converting enzyme (ECE) were tested using recombinant human ECE from CHO cells as described in Schmidt et al. (FEBS Letters 356, 1994: 238–243).

The enzyme preparations employed were, after membrane isolation and solubilization, further purified by Mono-Q chromatography and WGA lectin chromatography. The preparations obtained in this way contained no interfering foreign protease activities and had specific activities in the range 1–20 mU/mg. 5 µl of this enzyme solution were preincubated with 495 µl of test buffer (100 mM Pi, 500 mM NaCl, 0,1 mg/ml BSA pH 7.2) and with in each case 5 µl of appropriately concentrated solutions ($10^{-3}$ M, $10^{-4}$ M, $10^{-5}$ M etc.) of the inhibitors in the test buffer for 10 minutes. 50 µl aliquots were mixed with 5 µl of $2 \times 10^{-3}$ M Big ET1 solution (=Big Endothelin1) in 0.02% acetic acid. The mixtures were stopped after 1 hour at 37° C. by adding 150 µl of 0.5% TFA (=trifluoroacetic acid) in water, and centrifuged at 10000×g for 5 minutes, and the enzyme reaction was determined by measuring the endothelin formed by means of reversed phase HPLC as described in Takada et al. (Biochem. Biophys. Res. Comm. 176, 1991, 860), K. Ohnaka et al. (Biochem. Biophys. Res. Commun. 168, 1990, 1128). An inhibition plot was produced from the values of the inhibition at the various inhibitor concentrations, and the half-maximum inhibition (IC$_{50}$) was read off as a measure of the strength of the inhibitory effect. Table I shows the IC$_{50}$ values of the various substances for ECE, ACE and NEP 24.11.

TABLE I

| | IC$_{50}$ values for various inhibitors | | |
|---|---|---|---|
| Compounds | IC$_{50}$ (ECE) | IC$_{50}$ (ACE) | IC$_{50}$ (NEP) |
| 1a | 2 μm | >100 μm | >100 μm |
| 1b | 3 μm | >100 μm | >100 μm |
| 1e | 4 μm | >100 μm | >100 μm |

We claim:

1. A compound of the formula I:

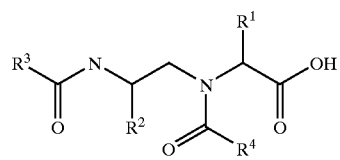

its physiologically active salts or combination thereof, where the substituents have the following meanings:

R$^1$ and R$^2$ independently of one another substituted or unsubstituted, branched or unbranched C$_1$–C$_8$-alkyl, C$_1$–C$_8$-alkylaryl or C$_1$–C$_8$-alkylhetaryl, substituted or unsubstituted aryl or hetaryl R$^3$ a group of the formula a

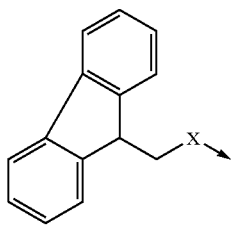

X = O, CH$_2$

R$^4$ substituted or unsubstituted C$_4$–C$_{14}$-aryl, C$_4$–C$_{14}$-hetaryl, with one or more rings containing one or more hetero atoms selected from the group of O, S and N, R$^5$ C$_1$–C$_8$-alkyl, C$_1$–C$_8$-alkylaryl, aryl or hetaryl.

2. A compound of the formula I, its physiologically active salts or combination thereof as defined in claim 1, wherein the substituents R$^1$ and R$^2$ are, independently of one another, substituted or unsubstituted, branched or unbranched C$_1$–C$_4$-alkyl, C$_1$–C$_4$-alkylaryl or C$_1$–C$_4$-alkylhetaryl, substituted or unsubstituted aryl or hetaryl.

3. A process for preparing a compound of the formula I as defined in claim 1, which comprises condensing a compound of the formula II:

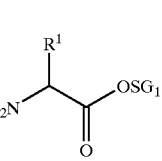

with a compound of the formula III:

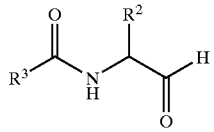

and reducing with a reducing agent to a compound of the formula IV:

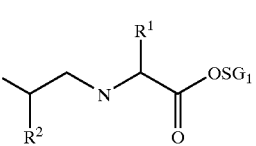

and reacting with an acylating agent R$^4$COCl (V) and eliminating the protective group SG$_1$ to give compounds of the formula I as defined in claim 1, where the substituents R$^1$, R$^2$, R$^3$ and R$^4$, have the meanings mentioned in claim 1, and SG$_1$ is a protective group.

4. A pharmaceutical preparation comprising a compound of the formula I, its physiologically active salts or combination thereof as defined in claim 1.

5. A combination of a pharmaceutical preparation as defined in claim 4 and at least one other active substance lowering blood pressure.

6. A combination as defined in claim 5 comprising ACE inhibitors as active substance lowering blood pressure.

7. A method for the inhibition of endothelin converting enzyme in a patient comprising administering a therapeutically effective amount of a compound of claim 1, its physiologically active salts or combinations thereof to a patient in need thereof.

8. The method of claim 7, wherein the patient has a disease selected from the group consisting of hypertension, pulmonary hypertension, myocardial infarct, chronic heart failure, angina pectoris, acute/chronic kidney failure, renal insufficiency, cerebral ischemia, subarachnoid hemorrhages, migraine, asthma, atherosclerosis, endotoxic shock, endotoxin-induced organ failure, intravascular coagulation, restenosis after angioplasty, benign prostate hyperplasia, ischemic and intoxication-induced kidney failure or hypertension, cyclosporin-induced kidney failure, metastasis and growth of mesenchymal tumors, cancer, contrast agent-induced kidney failure, pancreatitis and gastrointestinal ulcers.

9. The method of claim 7 for the selective inhibition of endothelin converting enzyme without inhibition of other proteases selected from the group of ACE, NEP, MMP-1, MMP-3, MMP-9, thermolysin, papain and thrombin.

10. The method of claim 7, wherein the compound of claim 1, its physiologically active salts or combinations thereof is administered in combination with other active substances which lower blood pressure.

* * * * *